(12) United States Patent
Chapples et al.

(10) Patent No.: US 7,279,080 B2
(45) Date of Patent: Oct. 9, 2007

(54) GAS SENSORS

(75) Inventors: John Chapples, Dorset (GB); Martin Geoffrey Jones, Hampshire (GB)

(73) Assignee: City Technology Limited, Portsmouth (GB)

( * ) Notice: Subject to any disclaimer, the term of this patent is extended or adjusted under 35 U.S.C. 154(b) by 819 days.

(21) Appl. No.: 10/343,162

(22) PCT Filed: Jul. 27, 2001

(86) PCT No.: PCT/GB01/03379

§ 371 (c)(1),
(2), (4) Date: Jul. 3, 2003

(87) PCT Pub. No.: WO02/11225

PCT Pub. Date: Feb. 7, 2002

(65) Prior Publication Data

US 2004/0026246 A1   Feb. 12, 2004

(30) Foreign Application Priority Data

Jul. 27, 2000   (EP) ................................ 00306383

(51) Int. Cl.
*G01N 27/407* (2006.01)
(52) U.S. Cl. ........................ 204/424; 204/431; 205/784
(58) Field of Classification Search ................ 204/424, 204/431, 432; 205/784, 781, 786.5, 787, 205/779.5; 429/33, 307
See application file for complete search history.

(56) References Cited

U.S. PATENT DOCUMENTS

| | | | |
|---|---|---|---|
| 3,969,285 A | * | 7/1976 | Grot ............................ 521/32 |
| 5,002,700 A | | 3/1991 | Otagawa et al. |
| 5,009,971 A | * | 4/1991 | Johnson et al. ............. 429/252 |
| 5,387,329 A | * | 2/1995 | Foos et al. ............. 204/403.06 |
| 5,466,575 A | * | 11/1995 | Cozzette et al. ................ 435/6 |
| 5,650,054 A | * | 7/1997 | Shen et al. .................. 204/412 |
| 5,919,583 A | | 7/1999 | Grot et al. |

FOREIGN PATENT DOCUMENTS

EP   0731520 A1   3/1996

(Continued)

OTHER PUBLICATIONS

Binesh, N & Bhat, S.V. Solid State Ionics 122 (1999) 291.

(Continued)

*Primary Examiner*—Kaj K. Olsen
(74) *Attorney, Agent, or Firm*—James B. Conte; Barnes & Thornburg LLP (57) ABSTRACT

This invention provides an assembly comprising a sensing electrode and a counter electrode in contact with a membrane body formed from a solid polymer electrolyte system comprising a fluorinated polymer matrix and a charge carrying component which is dispersed in the matrix the electrodes and membrane being housed in a housing having a gas diffusion barrier through which gas may flow. The charge carrying components are fluorinated organic proton conductors (such as heptadecafluorooctane sulphonic acid, bis-trifluoromethane sulphonamide, N-(2,6-diethylphenyl)-1,1,1-trifluoromethane sulphonamide, N-benzyltrifluoromethane sulphonamide and N, N-1,2-cyclohexanediylbis (1,1,1-trifluoromethane sulphonamide)). The polymer matrix is a homopolymer or copolymer of vinylidene fluoride preferably with fluorinated comonomers. The solid polymer electrolyte system preferably contains plasticising additive(s) and is cast as a coating onto one or more electrodes eg. Platinum gas diffusion electrodes forming an assembly for use in a gas sensor especially a CO sensor.

30 Claims, 7 Drawing Sheets

FOREIGN PATENT DOCUMENTS

| | | | |
|---|---|---|---|
| EP | 0872906 | A1 | 4/1998 |
| GB | 2094005 | | 1/1982 |
| GB | 2286889 | A | 2/1995 |
| JP | 08-171923 | * | 7/1996 |
| JP | 2001240742 | | 9/2001 |

OTHER PUBLICATIONS

Tarascon J.M. et al., Solid State Ionics, 86-88 (1996) 49.
Laconti, A.B. et al., ACS Publication' Chemical Hazards in the Workplace' (1981).
van der Wal, P.D. et al., Sensors & Actuators, B35-36 (1996) 199.
Chang, S. & Stetter, J.R. Electroanalysis, 2 (1990) 359.
Anantaraman A.V. & Gardner, C.L.J. Electroanaly. Chem., 414 (1996) 115.
Samec, Z. et al., Electroanalysis, 7 (1995) 1054.
Opekar, F. & Stulik, K., Anal. Chim. Acta 385 (1999) 151.
Yasuda A. et al. J. Electrochem. Soc. 139 (1992) 1091.
Otagawa, T. et al. Sensors & Actuators B1 (1990) 319.
Yasuda A. et.al., J. Electrochem. Soc. 139 (1992) 3224.
XP-002185389, Vij et al., abstract of Some Fluorine-containing nitrogen acids and their derivatives, 1997.
XP-002185387, 6001 Chemical Abstracts, Columbus, Ohio, US vol. 135, Abstract, 2001.
International Preliminary Examination Report from PCT/GB01/03379, date unavailble.
International Search report from PCT/GB01/03379, date unavailable.

* cited by examiner

GAS SENSORS

The present application is a national stage application of PCT/GB/01/03379, filed on Jul. 27, 2001.

This invention relates to assemblies for use in gas sensors comprising electrodes and a membrane formed of a solid polymer electrolyte and the use of the assemblies in toxic gas sensors.

In its simplest form, an electrochemical gas sensor consists of two electrodes (the anode and cathode) separated by an electrolyte. When the gas to be detected reacts at one of these electrodes, charge must be able to pass freely between the anode (where oxidation occurs) and the cathode (where reduction occurs) if the sensor's performance is not to be compromised. The electrolyte must therefore provide a highly conductive path through which charge is transported by ionic migration.

Traditionally, electrochemical sensors for detecting toxic gases at room temperature utilise liquid phase solutions of conducting ions as the electrolyte. This approach generally satisfies the requirement of a highly conducting medium between the electrodes and often also supplies a reactant species essential for the detection of the target gas. For example, in the CiTiceL (Trade Mark) carbon monoxide sensor, an aqueous solution of sulphuric acid provides the electrolyte, conferring both the high conductivity and water necessary for good sensor performance. Using carbon monoxide as an example of one of any number of gases that may undergo electrochemical oxidation, the general reactions occurring in the sensor may be illustrated by the following equations. At the working or sensing electrode (anode) carbon monoxide is electrochemically oxidised according to $$CO + H_2O \rightarrow CO_2 + 2H^+ + 2e^-$$

At the counter electrode (cathode) a reduction process must take place, for example the reduction of oxygen.

$$\tfrac{1}{2}O_2 + 2H^+ + 2e^- \rightarrow H_2O$$

The overall sensor cell reaction is the sum of these two electrode reactions, namely $$CO + \tfrac{1}{2}O_2 \rightarrow CO_2$$

It can be seen that there is no net consumption of water or other components of the electrolyte.

However, the use of liquid electrolytes in electrochemical gas sensors has certain disadvantages and imposes restrictions on their application. Leakage of electrolyte can be a significant problem, being hazardous to health and causing damage via corrosive action. The loss of this active component can also lead to degradation in sensor performance and premature failure. Consequently, considerable design effort and manufacturing cost are frequently incurred to overcome this vulnerability. Constraints on minimum sensor size are also imposed when using liquid electrolytes. Sensor volume is largely determined by the need to provide a sufficient reservoir of the electrolyte to meet the operating life and to accommodate mechanical wicking systems to ensure delivery of the electrolyte to the electrodes. Restrictions are also placed on the permissible operating temperatures (e.g. −20 to 55° C.) and humidities (e.g. 15 to 90% relative humidity) that such devices can tolerate whilst effectively maintaining the initial water balance of the liquid electrolyte. Extreme environments can lead to dehydration or flooding problems and produce electrolyte volume changes leading to sensor failure.

Recently, attempts have been made to overcome the inherent limitations of the liquid electrolyte by employing solid polymer electrolytes (SPEs). This technology offers significant advantages, not least the potential for reducing sensor complexity and cost. Numerous approaches have been adopted to overcome the major obstacles to implementing SPEs, namely their poor conductivities and/or their susceptibility to dehydration. One common technique is to utilise a fluorinated, ion-exchange polymer (Nafion) as the electrolyte [Otagawa, T. et al (1990); Yasuda, A. et al (1992); Opekar, F. & Stulik, K. (1999)]. For example, U.S. Pat. No. 5,573,648 uses Nafion 117 membranes or proton conducting metal oxide films (i.e. intrinsically conducting polymer structures) as the solid electrolyte in their gas sensors. This document describes a MEA of a two-electrode "sandwich" design to provide low cost amperometric sensors for detecting CO and other toxic gases. However, conduction within these membranes relies on the migration of the hydrated protons weakly associated with the sulphonic acid groups present on the fluorinated polymer backbone, therefore water remains an essential component without which their performance as SPEs is compromised [Samec, Z. et al (1995); Anantaraman, A. V. & Gardner, C. L. (1996); Yasuda, A. et al (1992)]. Consequently, the application of Nafion is effectively precluded in dry or high temperature environments with unhumidified sample gases. One typical approach employed to minimise this loss of ionic conductivity under desiccating conditions is to provide a water reservoir thereby keeping the membrane hydrated. [Chang, S. & Stetter, J. R. (1990); van derWal, P. D. et al (1996); LaConti, A. B. et al (1981)]. However, this approach is counter-productive and defeats some of the benefits of utilising SPEs namely reduced sensor complexity and cost.

An approach which has been widely adopted in the battery industry for avoiding liquid electrolyte is to rely on polymer systems infused with conducting salts and solvents or plasticisers [WO-A-98/04008]. Fluorinated polymers such as polyvinylidene fluoride (PVdF) have been impregnated with various alkali metal salts (commonly lithium) dissolved in high dielectric solvents [Tarascon, J. M et al (1996); WO-A-98/31064; WO-A-98/28812; GB-A-2309703] such as propylene carbonate or dimethyl formamide. In this manner, the reliance on a hydrated membrane for maintaining good ionic mobility is eliminated. Furthermore, the addition of specific non-volatile monomeric liquids (i.e. plasticisers) can improve ionic conductivity by reducing both polymer crystallinity and the glass-transition temperature, while increasing the relative permittivity of the system [Binesh, N. & Bhat, S. V. (1999)]. JP-A-171923 used fluorinated organic sulphonic acids dispersed within a fluorinated polymer matrix to produce proton conducting polymer electrolytes suitable for use in fuel cells capable of operating at high temperature such as 100-150° C. region and this system reduced the CO poisoning of the electrocatalyst. However, despite these attractive properties, such SPEs are not particularly amenable to direct implementation in sensors. The diverse nature and requirements of these two technologies effectively prevents the direct translation of a proven SPE formulation between them. For example, gas sensors by their nature cannot be sealed and must remain partially open to allow ingress of the atmosphere they will sense. Consequently, the use of any volatile electrolyte components that would eventually evaporate and degrade the SPE functionality is prohibited. Incompatibilities between the electrolyte solvent and sensor components, such as wetting of the PTFE membranes used in gas diffusion electrodes (for example by propylene carbonate) are also issues critical to gas sensors but not necessarily to batteries.

This invention provides an assembly for use in a gas sensor comprising a sensing electrode [2] and a counter electrode [6] each in contact with a membrane body formed from a solid polymer electrolyte (SPE) system [4] and a generally impermeable housing within which the electrodes and membrane are contained and a gas diffusion barrier through which gas is may diffuse from the exterior of the housing to the interior of the housing whereby the gas may contact the sensing electrode, wherein the SPE comprises a fluorinated polymer matrix and a charge carrying component which is dispersed and immobilised in the matrix and consists of a fluorinated organic proton conductor which is chemically compatible with the polymer.

The assembly may be incorporated into a gas sensor which additionally comprises means for measuring the flow of current or change in potential difference between the electrodes. Such gas sensors form part of the invention. The assembly may be prefabricated and supplied as a replaceable item for use with the apparatus comprising the said measuring means. The assembly itself may be formed from prefabricated components, such as pre-assembled membrane electrode assemblies (MEAs) comprising the electrodes and the SPE membrane. Other components of an assembly of the invention may include current collectors connected to the electrodes, seals against gas diffusion, mechanical connectors for connecting the assembly into the measuring apparatus, wick means to guide gas towards the sensing electrode, etc. The device may be as generally described in GB-A-2094005.

The SPE refers to the polymer matrix and the charge carrying component which are non-covalently bonded materials. The SPE system may also include other additives.

In the SPE system assembly of this invention, the proton bearing group is located on a molecule much smaller than the polymer matrix, the charge carrying component, which is fully compatible with the polymer matrix and is dispersed therein. The polymer itself is intrinsically non-conducting. The polymer matrix is non-ionic and/or non-ionisable which gives greater freedom of design for the acid host, allowing the removal of the proton to be rendered more facile and thereby improving the conductivity of the system. As used herein when the polymer matrix is referred to as non-ionic and/or non-ionisable this means normal use conditions.

The polymer of the SPE system used in this invention, may be a homopolymer of vinylidene fluoride (PVdF) or copolymer of vinylidene fluoride preferably with fluorinated comonomers, for instance a copolymer of vinylidene fluoride and hexafluoropropylene (HFP), trifluoroethylene ($VF_3$) or chlorotrifluoroethylene (CTFE).

Dispersed throughout the matrix of the polymer is a fluorinated organic proton conductor. The fluorinated organic proton conductor imparts conductivity and is chosen to be chemically compatible with the polymer matrix thereby giving a high degree of solubility of the fluorinated organic proton conductor in the solid polymer.

The organic proton conductor is preferably a fluorinated sulphonic acid, or a fluorinated-sulphonamide The sulphonic acid may have the general formula I:

(I)

where $R=[(CF_2)_nO_m(CF_2)_p]_qF$
in which n & p $\geq 0$
m=0 or 1, and
q=0 or an integer $\geq 1$.

A sulphonamide may have the general formula II (II)

in which $R^1$ is an electron withdrawing group having the general formula
$R^1=SO_2[(C_rH_xF_y)]$,
r=0 or an integer $\geq 1$, and x or y=0,
or are integers where x+y=2r+1;

$R^2$ is an electron withdrawing group in which $R^2=R^1$ or has the general structure $C_uH_sF_tR^3$, in which u=0 or is an integer $\geq 1$, and s or t=0, or are integers where s+t=2u;

$R^3$=H or F or is an aromatic, heteroaromatic, cycloalkyl or heterocycloalkyl group, having optional, preferably electron withdrawing groups attached.

The fluorinated organic proton conductor may be one or more of the following: heptadecafluorooctane sulphonic acid (Hepta), bis-trifluoromethane sulphonimide (Bis), N-(2, 6-diethylphenyl)-1,1,1-trifluoromethane sulphonamide, N-benzyltrifluoromethane sulphonamide, N,N-cyclohexane-1,2-diylbis(1,1,1-trifluoromethanesulphonamide) and perfluoro (2-ethoxyethane)sulphonic acid and N-ethylperfluorooctylsulphonamide.

The above mentioned novel SPE preferably has one or more additives added to it to give improved performance over the SPEs found in the prior art. An additive may have several properties: it may act as a plasticiser lowering the glass transition temperature and increasing the flexibility of the solid polymer and thus the electrolyte system; it may allow proton movement to occur and thereby enhance conductivity at ambient humidity and arrest the decline in membrane conductivity which might otherwise be demonstrated at reduced humidity; it may increase salvation of the fluorinated organic proton conductor in the matrix and increase the homogeneity of its dispersion. Separate compounds may confer one of these benefits, or a single compound may confer two or all three characteristics. The additives used in this invention may be one or more of the following; tetraethyleneglycol dimethyl ether (TEGDE), butyl sulphone (BS), polyethylene glycol 1000 (PEG 1000), polyoxyethylene (10) isooctylphenol ether (Triton X-100), dibutyl phthalate (DBP), 1-dodecyl-2-pyrrolidinone (DdP), dodecenyl succinic anhydride (DDSA) and undecanoic γ-lactone (UdL). Each additive should be non-volatile and preferably solid at room temperature.

The proportions of polymer matrix to fluorinated organic proton conductor in an effective SPE can vary. The fluorinated polymer is suitably present in an amount from 10 to 90 wt % whilst the fluorinated organic proton conductor is suitably present in an amount from 90 to 10 wt %. More preferably the fluorinated polymer is present in an amount from 25 to 75 wt % whilst the fluorinated organic proton conductor is present in an amount from 75 to 25 wt %.

The proportions of polymer matrix to fluorinated organic proton conductor plus additive(s) in an effective SPE can vary. The fluorinated polymer is suitably present in an amount from 10 to 90 wt %, whilst the fluorinated organic proton conductor plus additive(s) are suitably present in an amount from 90 to 10%. More preferably the fluorinated polymer is present in an amount from 25 to 75 wt %, whilst the fluorinated organic proton conductor plus additive(s) are present in an amount from 75 to 25 wt %. The weight ratio of the fluorinated proton conductor to additive(s) may vary from 10 to 100 wt %. We have found an optimum ratio for the components of the SPE system to be about 30 wt % fluorinated polymer, 40 wt % fluorinated organic proton conductor and 30 wt % additive when the polymer is poly(vinylidene fluoride-co-hexafluoropropylene), the acid is bis-trifluoromethane sulphonimide and the additive is butyl sulphone.

As mentioned above the electrode/solid polymer electrolyte combination excluding other sensor components may be referred to as membrane electrode assemblies (MEAs). These may be formed by standard film fabrication techniques or processes, such as those described in Davis, T. A., et al Opekar, F. & Štulík, K. (1999) patent applications EP-A-0731520, EP-A-0872906 and references therein. Alternatively solid or melt mixing and moulding processes may be used to fabricate a suitable MEA. In the present invention, the MEA may also be prepared by dissolving the fluorinated polymer and a fluorinated proton conductor in a suitable solvent system to form a casting liquid and forming the membrane, for instance by casting onto a substrate and subsequently removing the solvent. Preferably the solution further comprises the dissolved additive(s) as described above. The solution can be cast in an appropriate vessel to form a film following evaporation of the solvent. The resultant film (i.e. the membrane) may then be pressed between the two electrodes to form a MEA. Typically the thickness of the film may be between 5 and 1000 μm, although for optimum conductivity film thicknesses between 5 and 25 μm are preferable. Whilst the described embodiment uses free standing SPE films as described in the above method, it may also be desirable to cast the polymer electrolyte casting liquid onto a porous support to provide strength. The support material must be chemically compatible with the SPE solution. Examples of materials that may be suitable include PTFE, borosilicate glass fibre, and polypropylene. The solvent system may be one or more of a mixture of suitable ketones, ethers, esters, hydrocarbons, halocarbons or any other solvents or solvent systems in which the components of the polymer electrolyte are soluble. For convenience, it is preferable that the solvent(s) are volatile at standard temperature and pressures, although any other method of removing the solvent(s), such as heating at elevated temperatures, or under reduced pressures, or combinations of the above may be used.

The MEA described above may be used in conjunction with other components and electronic instrumentation to form an electrochemical sensor, that is capable of detecting gases or vapors that are susceptible to electrochemical oxidation or reduction at the sensing electrode, such as carbon monoxide, hydrogen sulphide, sulphur dioxide, nitric oxide, nitrogen dioxide, chlorine, hydrogen, hydrogen cyanide, hydrogen chloride, ozone, ethylene oxide, hydrides and oxygen. There are numerous possible arrangements of individual elements of the construction, but for convenience the principles are initially described with reference to a simple two electrode sensor configuration.

The two-electrode polymer MEA (FIG. 1) comprises a sensing electrode [2], proton conducting polymer electrolyte [4] and counter/reference electrode [6], with the SPE [4] interspersed between both electrodes forming a sandwich type configuration. The configuration is such that the catalyst from each individual electrode is in intimate contact with the polymer membrane. The membrane also acts as a separator and prevents direct electrical contact between the electrodes, thus preventing shorting. The solid nature of the polymer electrolyte obviates the need for conventional separators that serve the dual functions of preventing shorting between electrodes and acting as wicking materials in liquid electrolyte sensors. In this description of the invention, each electrode comprises a platinum black catalyst, intimately mixed with fine particles of polytetrafluoroethylene (PTFE) which acts as a binder and which also facilitates gaseous diffusion through the electrode. Support for the catalyst/PTFE structure is provided by a hydrophobic porous PTFE support [10].

Figure 1:
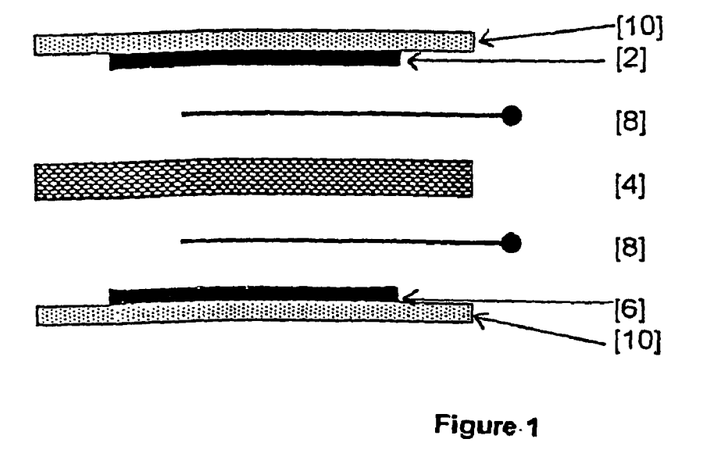
FIG. 1 is an exploded diagram of an example of a 2-electrode membrane electrode assembly (MEA) used in the assembly invention.

Electronic connection to the MEA is made via two platinum current collectors [8], each of which is in direct contact with one of the catalytic electrode surfaces. These provide connection with an external potentiostatic circuit which ensures a constant potential difference is maintained between the sensing electrode [2] and the counter/reference electrode [6], and which also converts the sensor's current signal to a voltage signal which can be related to the concentration of the gas being detected.

In the embodiment described above platinum black catalyst material [2 or 6] was chosen to facilitate the oxidation of carbon monoxide. It is preferable, although not necessary, to use a high surface area material for the catalyst, and in certain instances the catalyst electrode material may be solid in the form of a wire, ribbon or printed track. This material should also possess sufficient electronic conductivity to be able to support the flow of current generated during operation. Other nobel metal catalysts, such as gold, palladium, and ruthenium, their mixtures or alloys are also used. Other preferred electrode materials may include iridium, osmium, rhodium, silver, nickel, copper and carbon and alloys of the above combinations. The choice of catalyst is dictated by the nature of the analyte being detected, and any other gas(es) which are also present. By suitable choice it may be possible to discriminate the target analyte from other interferents, thus improving selectivity.

The MEA is enclosed in a housing (not shown) which acts as a protective body. In the most general and simple configurations, the housing needs only have an opening acting as the gas diffusion barrier. This enables gas ingress to the MEA by diffusion or convection. Preferably the assembly comprises suitable contacts to the MEA to provide electronic connection to external circuitry. The assembly may also comprise seals, or other mechanical connectors as a means of providing physical contact with external instrumentation. In the present invention, the gas diffusion barrier is an opening which has a defined geometry that imposes a diffusion limit on the rate of ingress of the analyte under detection. Under these circumstances the output of the sensor can be related to the external gas concentration through the known physical laws of diffusion. In the preferred design, this gas inlet capillary is protected from direct contact with the analyte sample, which may be contaminated with water droplets or other particulates, by a hydrophobic microporous PTFE membrane. This has sufficient porosity to minimise any bulk flow of gaseous species through the inlet capillary but does not interfere with gaseous diffusion. Other sensor designs may also incorporate an inboard filter to enhance the selectivity of the sensor by selectively removing interferents.

The SPE systems described above have been demonstrated within gas sensors using an amperometric two electrode carbon monoxide sensor. This technology is however amenable to incorporation into other sensor configurations. The two-electrode design was chosen as a test vehicle because of its simplicity, but the adoption of the SPE in sensor configurations with more than two electrodes, either in conventional or planar designs should prove feasible. Furthermore, this technology could also be adapted for use in gas sensors operating on potentiometric principles.

Figure 2:
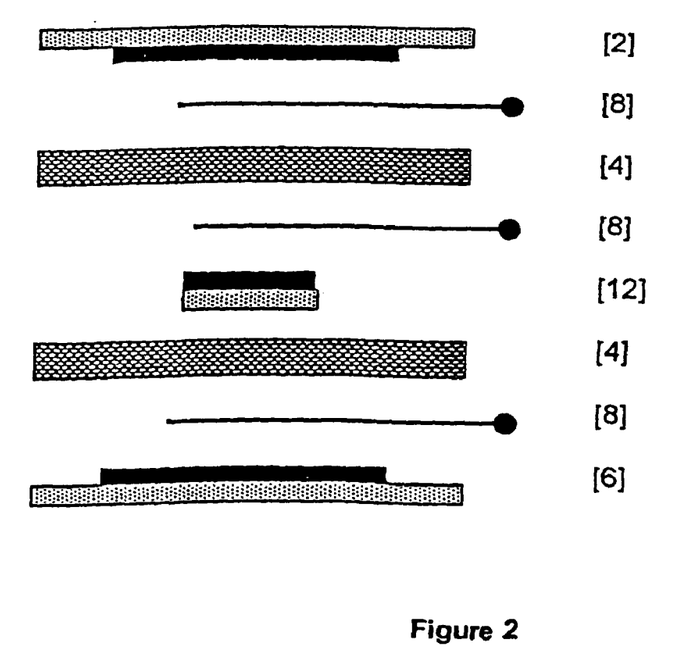
FIG. 2 is an exploded diagram of an example of a 3-electrode MEA useful in the invention.
Figure 3:
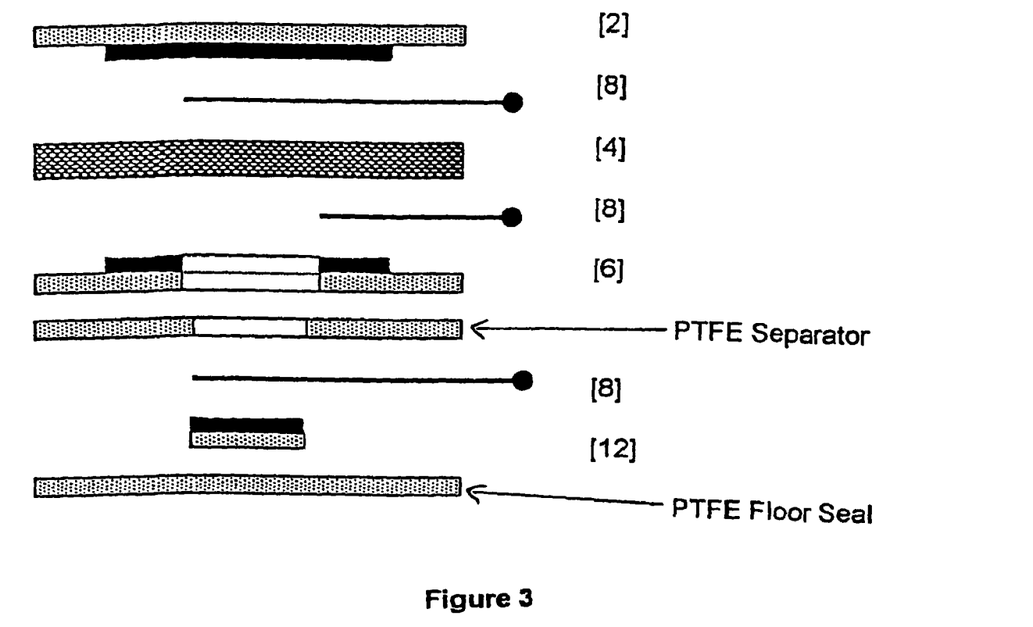
FIG. 3 is an exploded diagram of an alternative 3-electrode MEA useful in the invention.

Other configurations of the assembly of the invention may incorporate additional electrode assemblies including a reference electrode and scavenging electrode(s). The construction of these other electrode assemblies may be achieved in a similar manner to that described above for the two-electrode MEA. Two possible configurations for a sensor incorporating a reference electrode [12] are shown in FIGS. 2 and 3. However, it should be noted that the exact configuration is usually determined from consideration of several factors including optimisation of electrochemical performance and manufacturing considerations. Other configurations of MEA's may include multiple individual electrodes on a single porous support. For example it is possible to envisage a sandwich MEA configuration in which the sensing, counter and reference electrodes all have intimate contact with the same SPE.

Descriptions of the electrochemical assemblies have so far related to is designs in which the catalyst is supported on a porous backing PTFE material [10]. The non-liquid nature of the electrolyte means that alternative configurations are possible in which the SPE provides a suitable support for the catalyst. In this instance a sensor may be constructed whereby the catalyst is deposited directly onto the SPE.

Another possible configuration is where the catalytic electrode material is deposited onto a non-porous support. For example catalytic material may be screen printed or deposited by other means such as vapour deposition onto ceramic, glass, or inert plastics including PTFE, ABS and polypropylene. The SPE may then be deposited by any of the methods described above, as a thin film so as to cover the catalytic surface. As the substrate support material for the catalytic material is non-porous, diffusion to the catalytic surface necessarily occurs through the solid polymer electrolyte layer.

The use of such fluorinated organic proton conductors in addition to other additives has enabled some of the problems of the prior art to be overcome. The SPE provided is simple robust and amenable to mass production and suitable for use in toxic gas sensors and acidic oxygen sensors. The SPE system used in the current invention has high intrinsic conductivity and reduced reliance on hydration to sustain this conductivity. Using SPE in place of the aqueous acid in the sensor, the gaseous analyte or mixture to be detected on reaching the sensing electrode may react with molecules of water associated with the electrolyte or from the atmosphere. Charge flow through the SPE is mediated by the fluorinated organic proton conductor and aided by any additives present. The additives used in this invention have enhanced the conductivity of the solid polymer electrolyte and have reduced the decline in conductivity normally observed under desiccating conditions.

The invention will now be further described by way of non-limiting examples and with reference to the accompanying drawings.

EXAMPLE 1

SPEs were prepared by dissolving a copolymer of polyvinylidenefluoride-co-hexafluoropropylene (PVdF-HFP) copolymer in sufficient 2-butanone to give a 9 wt % solution.

Heptadecafluorooctanesulphonic acid (Hepta) was subsequently added to this solution to give a final loading of between 50-75 wt %. Membranes were cast from these solutions by controlled evaporation of the 2-butanone at ambient temperature, initially under atmospheric and then reduced pressure. The resultant films (ca. 5-25 µm thick) were cold pressed between a pair of platinum gas diffusion electrodes. The 75% Hepta membrane was incorporated in 2-electrode sensor hardware for characterisation tests in carbon monoxide (200 ppm in air). Sensors were connected to 3-electrode potentiostats (in which the counter and reference electrode terminals had been shorted together) and operated so that a zero potential difference was maintained across the sensing and counter electrodes. Following sufficient time for stabilisation of the output, each sensor was exposed in sequence to air for 5 minutes, 200 ppm CO/air for 5 minutes, and air again for a further 5 minutes. During this cycle, the sensor signal was logged continuously and the final response defined as the difference in output between the 5-minute signal in CO and the signal in air immediately prior to the analyte gas exposure.

Figure 4:
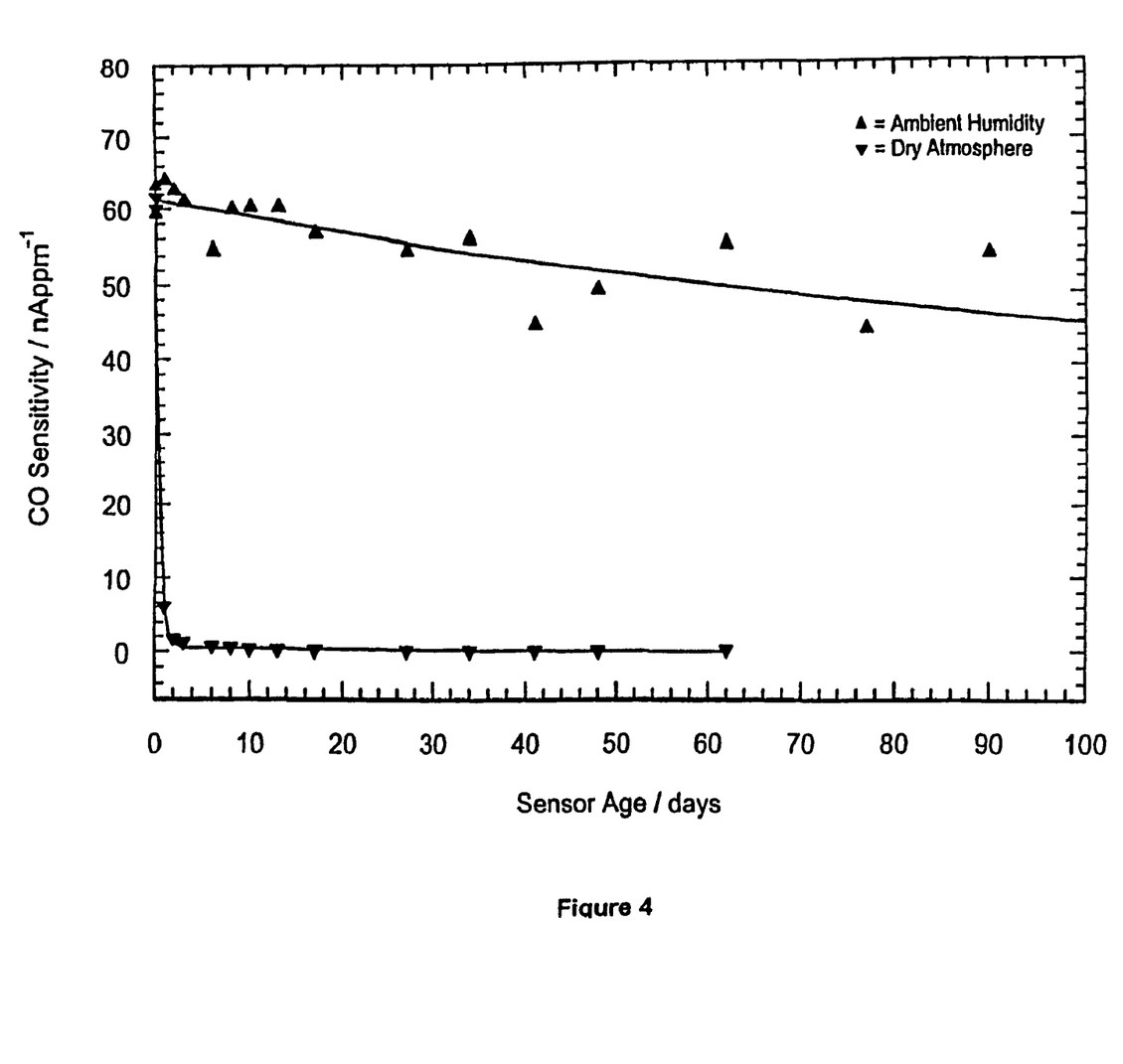
FIG. 4 shows results obtained from Example 1 (effect of ageing on the CO sensitivity of CTL 2-electrode sensors containing PVdF/hepta SPE).

FIG. 4 shows the effect of ageing on the CO sensitivity of a CiTiceL 2-electrode sensor containing 75% hepta in polyvinylidene fluoride-hexafluoro propylene (PVdF-HFP) solid polymer electrolyte at both ambient humidity and in a dry atmosphere. Tests revealed that the sensors based on Hepta/PVdF-HFP SPEs were capable of detecting ppm levels of CO. These devices initially demonstrated a satisfactory performance under ambient atmospheric conditions but partially lost sensitivity as they aged (FIG. 4). However, this rate of deactivation was even more severe under conditions of reduced humidity (i.e. relative humidity (RH)<10%). This novel solid polymer electrolyte showed a humidity dependent response and the following examples seek to avoid such a problem

EXAMPLE 2

The conductivities of SPE films with various additives were tested. The addition of additives to the SPE such as TEGDE, BS, PEG1000, Triton X-100, DBP, DdP, DDSA and UdL can significantly enhance conductivity under ambient conditions. SPE conductivities were calculated from the AC resistances (at 1 kHz) and membrane thicknesses determined using a modified micrometer fitted with gold contacts. Comparative measurements were initially made under ambient conditions (at known temperature and humidity)

and then, where appropriate, at a reduced humidity of 10% RH (again at ambient temperature). Samples were allowed to equilibrate for 48 hours under the conditions of attenuated humidity before the resistance measurements were made in situ. This phenomenon of enhanced conductivity was observed with both the Hepta (Table 1) and Bis (Table 2) loaded PVdF-HFP membranes. Furthermore, some of these additives, for example TEGDE, DdP, DDSA, and UdL, arrested the decline in membrane conductivity normally demonstrated at low atmospheric humidities (Table 3).

In the tables the proton conductor is referred to as an acid The extent of this improvement in performance is clearly coupled with the nature of the fluorinated organic proton conductor. Choice of additive also affects the properties. As a consequence of these observations three candidates, Hepta/TEGDE, Bis/UdL and Bis/BS were selected for evaluation with PVdF-HFP as solid polymer electrolytes in actual gas sensors in Example 3 below.

TABLE 1

Conductivity of PVdF-HFP Polymeric Films Cast with Hepta Fluorinated Organic Proton Conductor and Various Additives

| Additive | Film Composition Polymer: Acid: Additive wt % Ratio | Conductivity ($\mu$S/cm) |
| --- | --- | --- |
| Tetra(ethylene glycol) dimethyl ether (TEGDE) | 25:25:50 | 136.1 |
| Poly(ethylene glycol) 1000 (PEG 1000) | 25:25:50 | 121.1 |
| Dibutyl phthalate (DBP) | 25:25:50 | 94.8 |
| Polyoxyethylene(10) isooctylphenol ether (Triton X 100) | 25:25:50 | 72.4 |
| Zonyl (Trade Mark) FSN-100 (FSN100) | 25:25:50 | 37.2 |
| None | 75:25:0 | 0.48 |

TABLE 2

Conductivity of PvdF-HFP Polymeric Films Cast with Bis Fluorinated Organic Proton Conductor and Various Additives

| Additive | Film Composition Polymer: Acid: Additive wt % Ratio | Conductivity ($\mu$S/cm) |
| --- | --- | --- |
| Butyl sulphone (BS) | 34:33:33 | 276.1 |
| 1-Dodecyl-2-pyrrolidinone (DdP) | 34:33:33 | 99.1 |
| Undecanoic $\gamma$-lactone (UdL) | 34:33:33 | 58.6 |
| Dodecenylsuccinic anhydride (DDSA) | 34:33:33 | 35.1 |
| Poly(ethylene glycol) 2-[ethyl[(heptadecafluorooctyl)sulphonyl]amino]ethyl methyl ether (PEGEHSA) | 34:33:32 | 20.9 |
| None | 50:50:0 | 18.4 |

TABLE 3

Change in Conductivity with Humidity of PvdF-HFP Polymeric Films Containing Hepta or Bis Fluorinated Organic Proton Conductors Cast with Various Additives

| Acid | Additive | Film Composition Polymer: Acid: Additive wt % Ratio | Conductivity Change (%) between 25→7% RH |
| --- | --- | --- | --- |
| Hepta | Tetra(ethylene glycol) dimethyl ether | 25:25:50 | +9 |
| Hepta | 1-Dodecyl-2-pyrrolidinone | 34:33:33 | −16 |
| Hepta | Dodecenylsuccinic anhydride | 34:32:34 | −39 |
| Hepta | Undecanoic $\gamma$-lactone | 34:33:33 | −65 |
| Hepta | None | 51:49:0 | −99 |
| Bis | Undecanoic $\gamma$-lactone | 34:33:33 | +76 |
| Bis | Tetra(ethylene glycol) dimethyl ether | 25:25:50 | −7 |
| Bis | Butyl sulphone | 34:33:33 | −21 |
| Bis | None | 50:50:0 | −100 |

EXAMPLE 3

SPEs were prepared by dissolving PVdF-HFP copolymer in sufficient 2-butanone to give a 9 wt % solution. The fluorinated organic proton conductor and additive were subsequently added to this solution to give a final loading of 33 wt % as specified in the Table. Conducting membranes were cast from these solutions by controlled evaporation of the 2-butanone at ambient temperature, initially under atmospheric and then reduced pressure. The resultant films (ca. 5-25 $\mu$m thick) were cold pressed between a pair of platinum gas diffusion electrodes and subsequently incorporated into (CiTiceL) 2-electrode sensor hardware for characterisation tests in carbon monoxide (200 ppm in air). The sensor test method is as described in Example 1.

Figure 5:
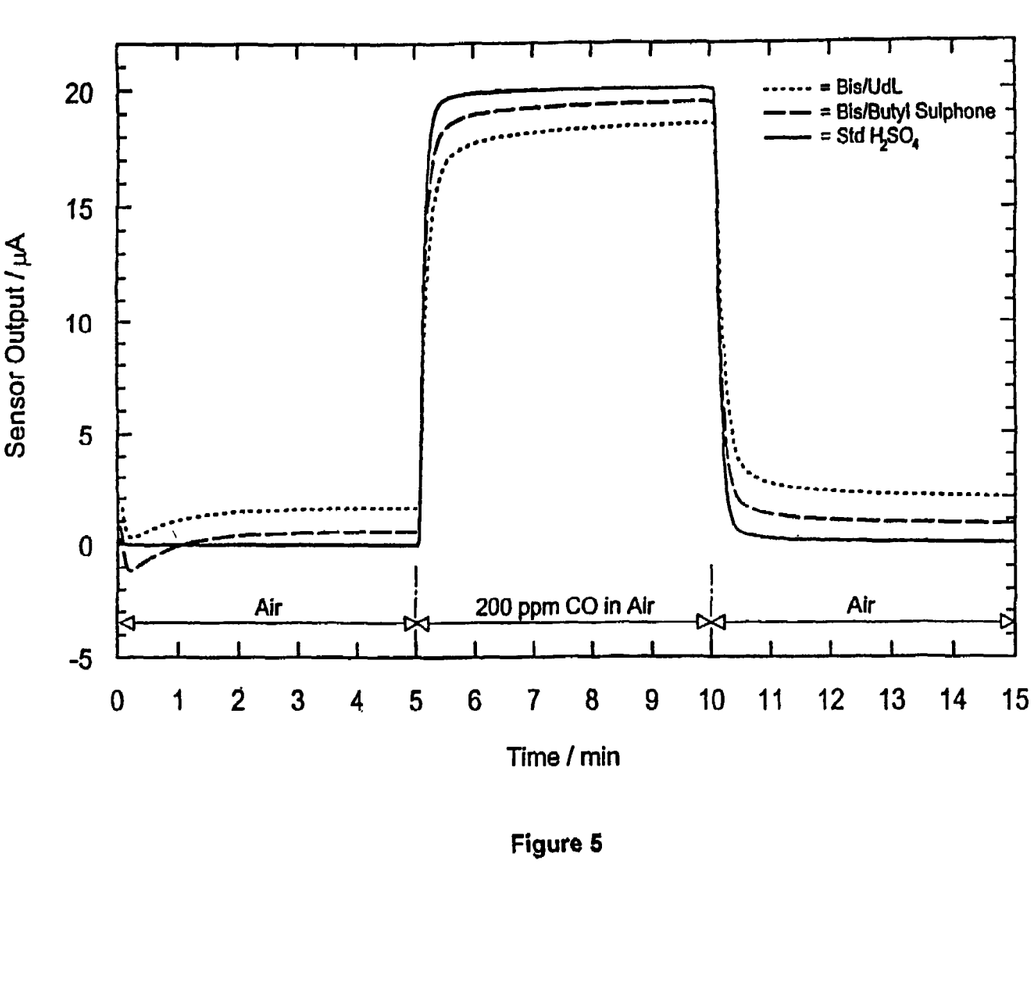
FIG. 5 shows results obtained from Example 3 (carbon monoxide response of CTL 2-electrode sensors containing various solid and liquid electrolytes).

FIG. 5 illustrates the response of Bis/UdL and Bis/BS 2-electrode sensors to the addition of 200 ppm CO (added at the 5 min stage) compared with a control sensor containing a liquid electrolyte of 5M sulphuric acid (Std 5M $H_2SO_4$).

Figure 6:
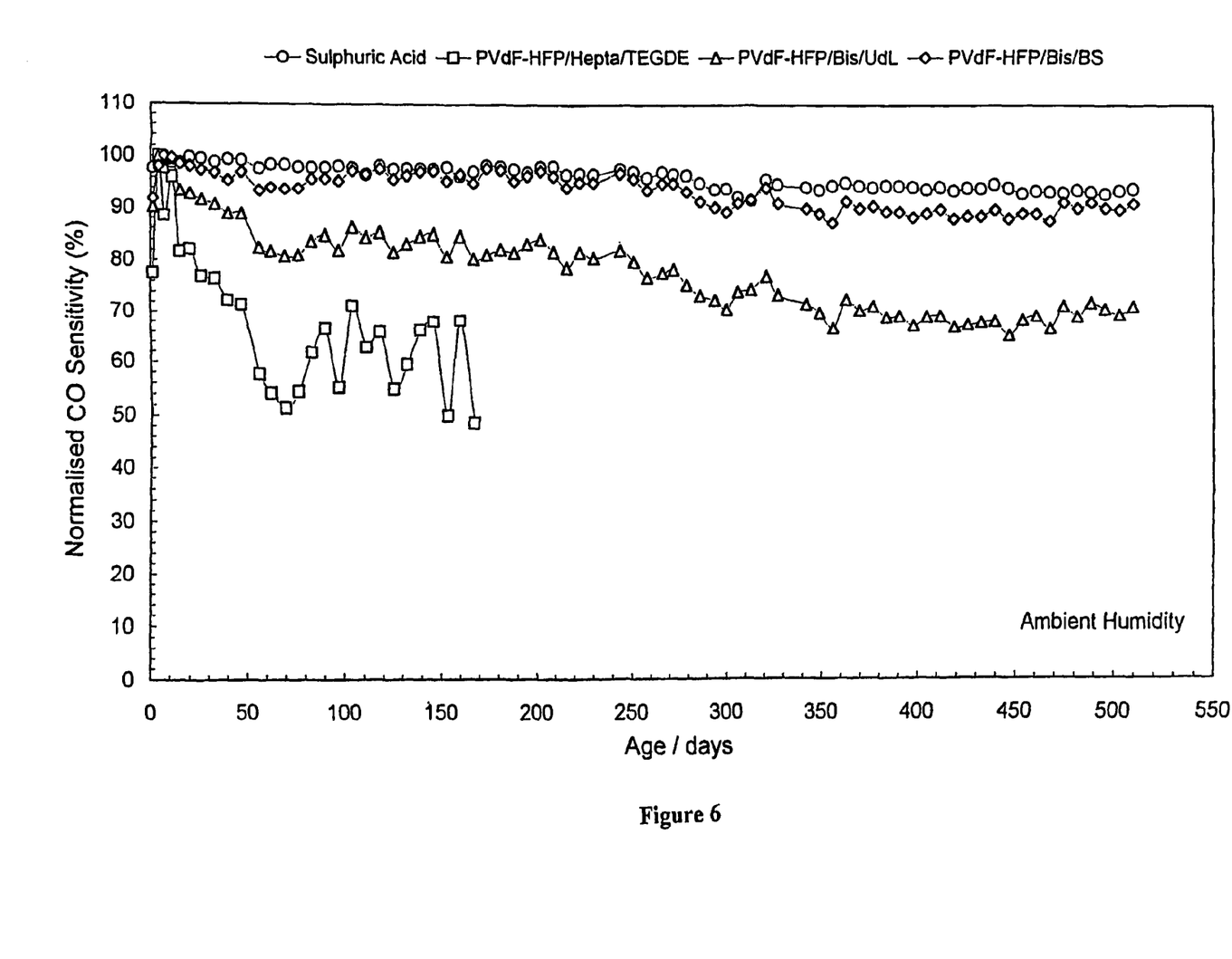
FIG. 6 shows results obtained from Example 3 (effect of ageing under ambient conditions on the CO sensitivity of CTL 2-electrode sensors containing various solid and liquid electrolytes).

FIG. 6 shows the effect of ageing under ambient conditions on the CO sensitivity of 2-electrode sensors with different solid polymer electrolyte systems.

Figure 7:
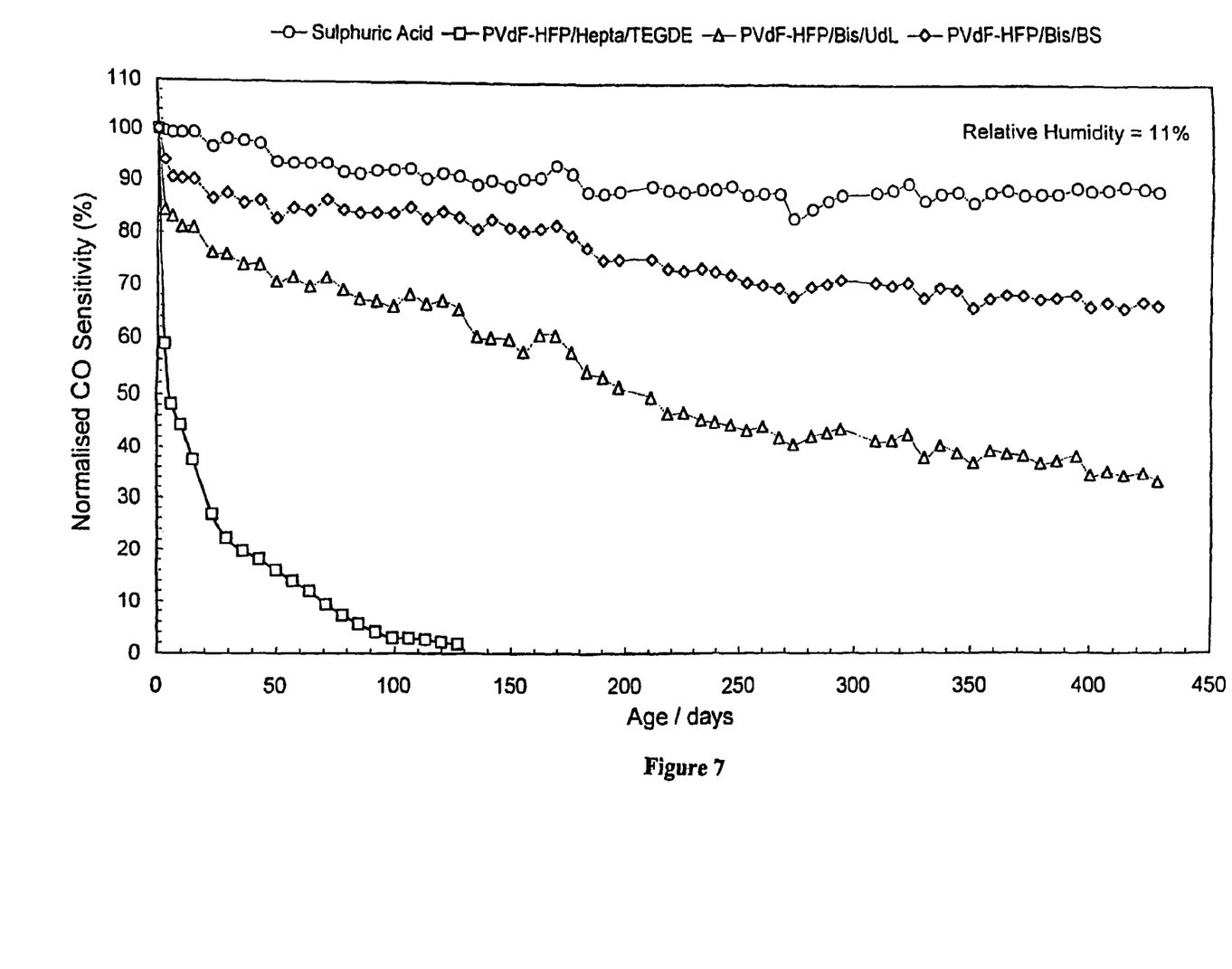
FIGS. 7 and 8 show results obtained from Example 3 (effect of ageing under attenuated and elevated humidities (respectively) on the CO sensitivity of CTL 2-electrode sensors containing various solid and liquid electrolytes).
Figure 8:
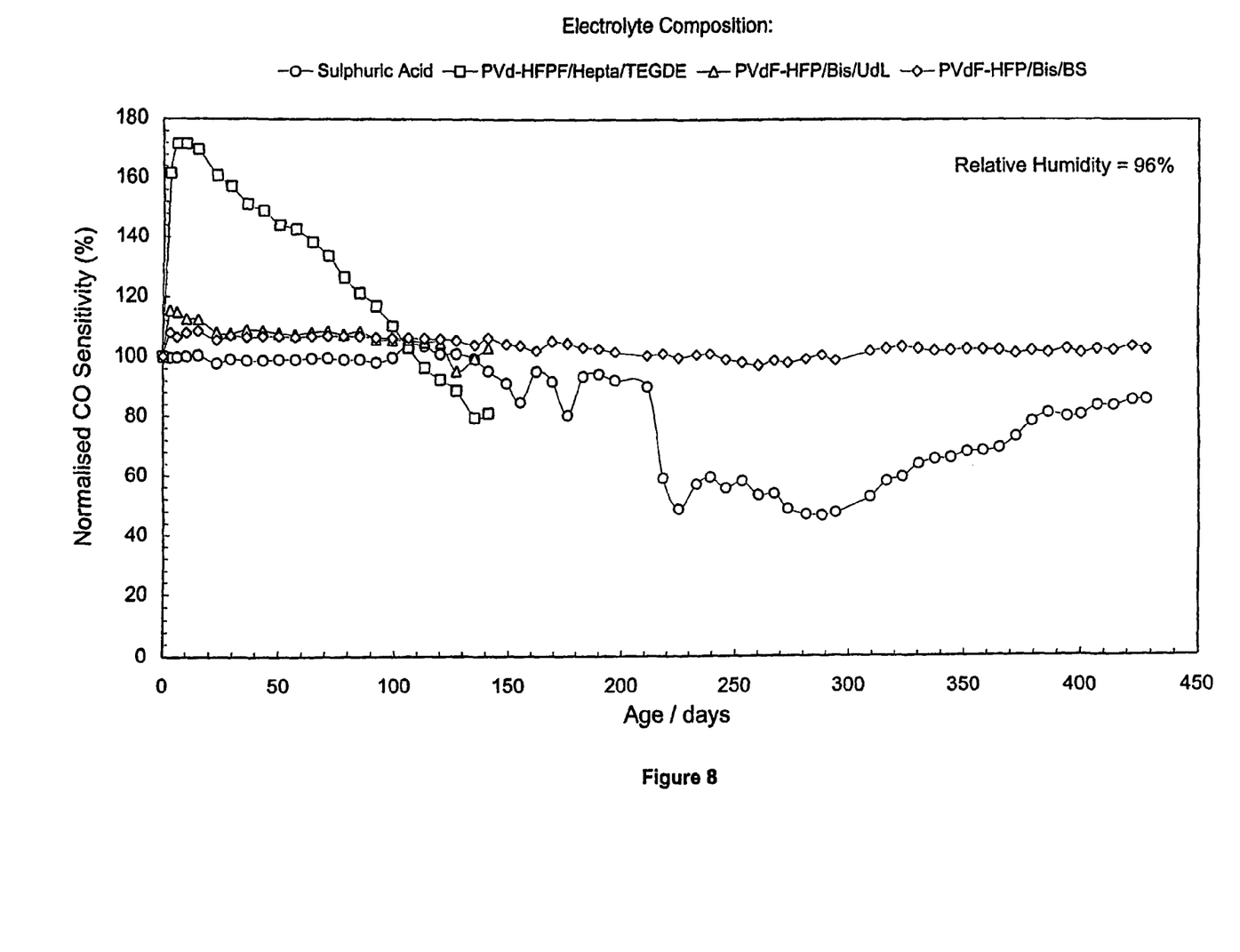

FIG. 7 shows the effect of ageing under reduced humidity on the CO sensitivity of 2-electrode sensors with different solid polymer electrolyte systems, whilst FIG. 8 shows the effect of ageing under elevated humidity conditions.

Tests on these sensors demonstrated that favourable performance characteristics were obtainable with SPEs based on Bis and butyl sulphone or undecanoic $\gamma$-lactone additives. Benchmarked against standard controls containing a liquid electrolyte of sulphuric acid, these devices displayed fast responses and high CO sensitivities (but initially had relatively high air baseline signals) (FIG. 5). Reasonable stability was also displayed as these sensors aged in air under normal ambient conditions (FIG. 6). Under an atmosphere of reduced humidity (ca 15% RH), sensors based on both Bis/UdL and Bis/BS SPE suffered only limited deactivation as a result of dehydration (FIG. 7). In contrast, when operated at elevated humidity (ca. 95% RH) marginal improvements in performance were obtained (FIG. 8).

REFERENCES

Anantaraman A. V. & Gardner, C. L. J. Electroanal. Chem., 414 (1996) 115.

Binesh, N & Bhat, S. V. Solid State Ionies 122 (1999) 291.

Chang, S. & Stetter, J. R. Electroanalysis, 2 (1990) 359.

Davis, T. A., Genders, J. D. & Pletcher, D. The Electrochemical consultancy (pubs) (1997) "A First Course in Ion Permeable Membranes"

EP-A-0731520

EP-A-0872906

Laconti, A. B. et al., ACS Publication 'Chemical Hazards in the Workplace' (1981) 551.

Opekar, F. & Stulik, K., Anal. Chim. Acta 385 (1999) 151.

Otagawa, T. et al Sensors & Actuators B1 (1990) 319.

Samec, Z. et al., Electroanalysis, 7 (1995) 1054.

Tarascon J. M. et al., Solid State Ionics, 86-88 (1996) 49.

van der Wal, P. D. et al., Sensors & Actuators, B35-36 (1996) 119.

Yasuda A. et al., J. Electrochem. Soc. 139 (1992) 3224.

Yasuda A. et al. J. Electrochem. Soc. 139 (1992) 1091.

The invention claimed is:

1. An assembly for use in a gas sensor comprising a sensing electrode and a counter electrode each in contact with a membrane body formed from a solid polymer electrolyte (SPE) system and a generally impermeable housing within which the electrodes and membrane are contained and a gas diffusion barrier through which gas may diffuse from the exterior of the housing to the interior of the housing whereby the gas may contact the sensing electrode, wherein the SPE comprises a fluorinated polymer matrix and a charge carrying component which is dispersed and non-covalently immobilized in the polymer matrix and consists of a fluorinated organic proton conductor which is chemically compatible with the polymer.

2. The assembly according to claim 1 wherein the polymer of the SPE system is non-ionic.

3. The assembly according to claim 1 in which the polymer of the SPE system is a homopolymer or copolymer of vinylidene fluoride.

4. The assembly according to claim 3 in which the polymer of the SPE system is a copolymer of vinylidene fluoride and a compound selected from the group consisting of hexafluoropropylene, trifluoroethylene and chlorotrifluoroethylene.

5. The assembly according to claim 1 in which the fluorinated proton conductor of the SPE system is a fluorinated sulphonic acid or fluorinated sulphonamide.

6. The assembly according to claim 5 in which the conductor is a sulphonic acid having the general formula I:

(I)

where $R=[(CF_2)_nO_m(CF_2)_p]_qF$ in which n & p $\geq$ 0, m=0 or 1, and q=0 or an integer $\geq$ 1.

7. The assembly according to claim 5 in which the conductor is a sulphonamide having the general formula II.

(II)

in which $R^1$ is an electron withdrawing group having the general formula $R^1 = SO2[(C_rH_xF_y)_r]$ r=0 or an integer $\geq$ 1, and x or y =0, or are integers where x+y=2r+1;

$R^2$ is an electron withdrawing group in which $R_2=R^1$ or has the general 15 structure $C_uH_sF_tR^3$, in which u=0 or is an integer $\geq$ 1, and s or t=0, or are integers where s+t=2u;

$R_3$=H or F or is an aromatic, heteroaromatic, cycloalkyl or heterocycloalkyl group.

8. The assembly according to claim 7, wherein the aromatic, heteroaromatic, cycloalkyl or heterocylcoalkyl group at R3 has electron withdrawing groups attached.

9. The assembly according to claim 5 in which the fluorinated organic proton conductor of the SPE system is one or a mixture of heptadecafluorooctane sulphonic acid, bistrifluoromethane sulphonimide, -(2,6-diethylphenyl)-1,1,1 -trifluoromethanesulphonarmide, -benzyltrifluoromethanesulphonamide and, N, N'-cyclohexanel ,2 diylbis (1,1,1-trifluromethanesulphonamide), perfluoro-(2-ethoxyethane)sulphonic acid and N-ethyl perfluorooctylsulphonamide.

10. The assembly according to claim 1 in which the SPE system comprises one or more additive(s) selected from the group consisting of tetraethylene glycol dimethyl ether (TEGDE), butyl sulphone (BS), poly(ethylene glycol) 1000 (PEG1000), polyoxyethylene (10) isooctylphenol ether (Triton X-100), dibutyl phthalate (DBP), 1-dodecyl-2-pyrrolidinone (DdP),dodecenylsuccinic anhydride (DDSA) and undecanoic y-lactone (UdL).

11. The assembly as claimed in claim 10 in which in the SPE system the total amount of fluorinated organic proton conductor plus additive is from 10 to 90 wt % based on the total weight of the system.

12. The assembly as claimed in claim 11, wherein the total amount of fluorinated organic proton conductor plus additive is from 25 to 75 wt % based on the total weight of the system.

13. The assembly as claimed in claim 1 in which in the SPE sytem the amount of fluorinated organic proton conductor is in the range 10 to 90 wt % based on the total weight of polymer plus proton conductor.

14. An assembly according to claim 1 wherein the sensing electrode is a gas diffusion electrode.

15. An assembly according to claim 14 in which the sensing electrode to comprises a high surface area catalyst.

16. The assembly according to claim 1 wherein the sensing electrode is formed from a metal selected from the group consisting of platinum, gold, palladium, ruthenium, iridium, osmium, rhodium, silver, nickel, copper, carbon and their mixture and alloys.

17. The assembly according to claim 16 wherein the metal is in the form of a wire, ribbon or track.

18. The assembly of claim 1 which also comprises a reference electrode and/or a scavenging electrode.

19. A gas sensor comprising an assembly for use in a gas sensor comprising a sensing electrode and a counter electrode each in contact with a membrane body formed from a solid polymer electrolyte (SPE) system and a generally impermeable housing within which the electrodes and membrane are contained and a gas diffusion barrier through which gas may diffuse from the exterior of the housing to the interior of the housing whereby the gas may contact the sensing electrode, wherein the SPE comprises a fluorinated polymer matrix and a charge carrying component which is dispersed and non-covalently immobilized in the polymer matrix and consists of a fluorinated organic proton conductor which is chemically compatible with the polymer and a means for measuring flow of current or changes in potential difference between the sensing and counter electrodes.

20. A method of detecting a gaseous component in a gaseous sample by utilizing a gas sensor according to claim 19 in which the sample is contacted with the gas diffusion barrier whereby the component diffuses into the housing and contacts the sensing electrode where the gaseous component reacts in an electochemical reaction whereby charge flows through the solid polymer electrolyte and is detected as an indicator of the presence of the gaseous component.

21. A method according to claim 20, in which the gaseous component to be detected is a gas that undergoes electro-oxidation or electro-reduction and is selected from the group consisting of carbon monoxide, hydrogen sulphide, sulphur dioxide, nitric dioxide, nitrogen dioxide, chlorine, hydrogen, hydrogen cyanide, hydrogen chloride, ozone, ethylene oxide, a hydride and oxygen.

22. A method according to claim 21, wherein the gas that undergoes electro-oxidation or electro-reduction is carbon monoxide.

23. An assembly for use in a gas sensor comprising a sensing electrode and a counter electrode each in contact with a membrane body formed from a solid polymer electrolyte (SPE) system and a generally impermeable housing within which the electrodes and membrane are contained and a gas diffusion barrier through which gas may diffuse from the exterior of the housing to the interior of the housing whereby the gas may contact the sensing electrode, wherein the SPE comprises a fluorinated polymer matrix and a charge carrying component which is dispersed and non-covalently immobilized in the polymer matrix which is a homopolymer or copolymer of vinylidene fluoride and consists of a fluorinated organic proton conductor which is chemically compatible with the polymer.

24. An assembly for use in a gas sensor comprising a sensing electrode and a counter electrode each in contact with a membrane body formed from a solid polymer electrolyte (SPE) system and a generally impermeable housing within which the electrodes and membrane are contained and a gas diffusion barrier through which gas may diffuse from the exterior of the housing to the interior of the housing whereby the gas may contact the sensing electrode, wherein the SPE comprises a fluorinated polymer matrix and a charge carrying component which is dispersed and non-covalently immobilized in the polymer matrix and consists of a fluorinated organic proton conductor which is chemically compatible with the polymer and is a fluorinated sulphonic acid or fluorinated sulphoriamide.

25. An assembly according to claim 12 or 24, wherein the polymer is a copolymer of vinylidene fluoride and a compound selected from the group consisting of hexafluoropropylene, trifluoroethylene and chlorotrifluoroethylene.

26. An assembly for use in a gas sensor comprising a sensing electrode and a counter electrode each in contact with a membrane body formed from a solid polymer electrolyte (SPE) system and a generally impermeable housing within which the electrodes and membrane are contained and a gas diffusion barrier through which gas may diffuse from the exterior of the housing to tbe interior of the housing whereby the gas may contact the sensing electrode, wherein the SPE comprises a fluorinated polymer matrix which is a homopolymer or copolymer of vinylidene fluoride and a charge carrying component which is dispersed and non-covalently immobilized in the polymer matrix and is a fluorinated sulphonic acid or fluorinated sulphonamide.

27. An assembly according to claim 26, wherein the SPE system comprises one or more additive(s) selected from the group consisting of tetraethylene glycol dimethyl ether (TEGDE), butyl sulphone (BS), poly(ethylene glycol) 1000 (PEGI000), polyoxyethylene (10) isooctylphenol ether (Triton X-100), dibutyl phthalate (DBP), 1-dodecyl-2-pyrrolidinone (DdP), dodecenylsuccinic anhydride (DDSA) and undecanoic y-lactone (UdL).

28. An assembly according to claim 27, wherein in the SPE system the total amount of fluorinated organic proton conductor plus additive is from 10 to 90 wt % based on the total weight of the system.

29. An assembly according to claim 28, wherein the total amount of fluorinated organic proton conductor plus additive is from 25 to 75 wt % based on the total weight of the system.

30. A method of detecting carbon monoxide in a gaseous sample by utilizing a gas sensor comprising a sensing electrode and a counter electrode each in contact with a membrane body formed from a solid polymer electrolyte (SPE) system and a generally impermeable housing within which the electrodes and membrane are contained and a gas diffusion barrier through which gas may diffuse from the exterior of the housing to the interior of the housing whereby the gas may contact the sensing electrode, wherein the SPE comprises a fluorinated polymer matrix which is a homopolymer or copolymer of vinylidene fluoride and a charge carrying component which is dispersed and non-covalently immobilized in the polymer matrix and is a fluorinated sulphonic acid or fluorinated sulphonamide and a means for measuring flow of current or changes in potential difference between the sensing and counter electrodes, in which the sample is contacted with the gas diffusion barrier whereby the carbon monoxide diffuses into the housing and contacts the sensing electrode where the gaseous component reacts in an electochemical reaction whereby charge flows through the solid polymer electrolyte and is detected as an indicator of the presence of the carbon monoxide.

* * * * *